(12) United States Patent
Lina et al.

(10) Patent No.: US 7,611,500 B1
(45) Date of Patent: Nov. 3, 2009

(54) WOUND THERAPY DEVICE AND RELATED METHODS

(75) Inventors: Cesar Z. Lina, Universal City, TX (US); Keith Heaton, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 1309 days.

(21) Appl. No.: 08/951,832

(22) Filed: Oct. 16, 1997

Related U.S. Application Data

(63) Continuation of application No. 08/517,901, filed on Aug. 22, 1995, now abandoned, which is a continuation-in-part of application No. 08/293,854, filed on Aug. 22, 1994, now abandoned.

(51) Int. Cl.
*A61F 13/00* (2006.01)
*A61F 13/02* (2006.01)
*A61M 1/06* (2006.01)

(52) U.S. Cl. .................... 604/305; 604/73; 604/304; 604/307

(58) Field of Classification Search .............. 604/289, 604/290, 304, 327, 356, 406, 319, 347, 21, 604/317–323, 305, 307; 606/131; 128/760
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,257 A | 1/1961 | Simmons |
| 3,026,874 A | 3/1962 | Stevens |
| 3,066,672 A | 12/1962 | Crosby, Jr. et al. |
| 3,367,332 A | 2/1968 | Groves |
| 3,520,300 A | 7/1970 | Flower et al. ............ 128/276 |
| 3,568,675 A | 3/1971 | Harvey ................. 128/275 |
| 3,648,692 A | 3/1972 | Wheeler |
| 3,682,180 A | 8/1972 | McFarlane |
| 3,804,090 A * | 4/1974 | Holbrook ............... 604/319 |

(Continued)

FOREIGN PATENT DOCUMENTS

AU      550575 A1    8/1982

(Continued)

OTHER PUBLICATIONS

S.E. Greer, "Whither Subatmospheric Pressure Dressing," The Institute of Plastic Surgery, The New York University Medical Center, pp. 1-10.

(Continued)

*Primary Examiner*—Tatyana Zalukaeva
*Assistant Examiner*—Melanie J Hand

(57) ABSTRACT

A wound closure apparatus is disclosed which includes a housing that contains a vacuum pump and a chamber for holding a disposable wound fluid collection canister. The canister resides within the chamber and connects at an outlet with the vacuum pump and at an inlet with a pad. The pad is placed over a wound and adhesively secured thereto. When the vacuum pump activates, it evacuates air from the canister resulting in wound fluids flowing from the wound into the canister. After the canister is filled, it is removed from the chamber and replaced with another canister to continue the removal of wound fluids.

17 Claims, 12 Drawing Sheets

U.S. PATENT DOCUMENTS

| | | |
|---|---|---|
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,402,687 A * | 9/1983 | Denty et al. ............... 604/319 |
| 4,419,097 A | 12/1983 | Rowland |
| 4,460,361 A * | 7/1984 | Nichols ...................... 604/319 |
| 4,460,369 A * | 7/1984 | Seymour .................... 424/448 |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,605,400 A * | 8/1986 | Kurtz et al. .................. 604/319 |
| 4,608,041 A | 8/1986 | Nielson |
| 4,627,833 A | 12/1986 | Cook |
| 4,631,061 A * | 12/1986 | Martin ........................ 604/327 |
| 4,640,688 A | 2/1987 | Hauser |
| 4,655,754 A | 4/1987 | Richmond et al. |
| 4,664,662 A | 5/1987 | Webster |
| 4,710,165 A * | 12/1987 | McNeil et al. ................ 604/67 |
| 4,733,659 A | 3/1988 | Edenbaum et al. |
| 4,735,610 A | 4/1988 | Akkas et al. |
| 4,743,232 A * | 5/1988 | Kruger ........................ 604/180 |
| 4,747,166 A * | 5/1988 | Kuntz ........................... 604/437 |
| 4,758,220 A | 7/1988 | Sundblom et al. |
| 4,787,888 A | 11/1988 | Fox |
| 4,826,494 A | 5/1989 | Richmond et al. |
| 4,834,110 A | 5/1989 | Richard ...................... 128/760 |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,886,502 A * | 12/1989 | Poirier et al. ................ 604/175 |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,028,355 A * | 7/1991 | Cope et al. .................. 252/500 |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,234,419 A * | 8/1993 | Bryant et al. ............... 604/320 |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A * | 8/1995 | Todd et al. .................. 604/317 |
| 5,466,229 A * | 11/1995 | Elson et al. .................. 604/317 |
| 5,527,293 A | 6/1996 | Zamierowski |
| 5,549,584 A * | 8/1996 | Gross .......................... 604/319 |
| 5,556,375 A | 9/1996 | Ewall |
| 5,607,388 A | 3/1997 | Ewall |
| 5,636,643 A | 6/1997 | Argenta et al. ............. 128/897 |
| 5,645,081 A | 7/1997 | Argenta et al. |
| 5,678,564 A * | 10/1997 | Lawerance et al. .......... 604/331 |
| 6,071,267 A | 6/2000 | Zamierowski |
| 6,135,116 A | 10/2000 | Vogel et al. |
| 6,142,982 A * | 11/2000 | Hunt et al. ................... 604/313 |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 28 09 828 | 9/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0 358 302 | 3/1990 |
| EP | 0358302 A2 | 3/1990 |
| EP | 0 601 313 A2 | 6/1994 |
| EP | 0 620 720 B1 | 3/1998 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/11795 | 4/1990 |
| WO | WO 90/10424 | 9/1990 |
| WO | 9309736 * | 5/1993 |
| WO | WO 93/09727 | 5/1993 |
| WO | WO 94/20041 | 9/1994 |
| WO | WO 96/05873 | 2/1996 |
| WO | WO 97/18007 | 5/1997 |

| | | |
|---|---|---|
| WO | WO 99/13793 | 3/1999 |

OTHER PUBLICATIONS

L.C. Argenta et al., "Vacuum-Assisted Closure: A New Method for Wound Control and Treatment: CLinical Experience," Annals of Plastic Surgery, vol. 38 No. 6, pp. 563-576, Jun. 1997.

M.J. Morykwas, PhD et al., "Vacuum-Assisted Closure: A New Method for Wound Control and Treatment: Animal Studies and Basic Foundation," Annals of Plastic Surgery, vol. 38 No. 6, Jun. 1997, pp. 553-562.

Iu. A. Davydov et al. "Vacuum Therapy in the Treatment of Acute Purulent Diseases of Soft Tissues and Purulent Wounds," Department of General Surgery of the Yaroslavl State Institute of Medicine, Nov. 1986, pp. 43-46, (Translation).

Iu. A. Davydov et al., "Vacuum Therapy in the Prevention of Postoperative Wound Infection," Department of General Surgery of the Yaroslavl Institute of Medicine, Nov. 1990, pp. 91-95, Translation of Document.

N.I. Iankov, "Stimulation of the Consolidation of Mandibular Fractures by Means of Vacuum Therapy," Stomatologiia (Moscow), vol. 50, No. 5, p. 86, 1971, Translation of Document.

I. M. Inoiatov et al., "Vacuum Aspiration in the Treatment of Perineal Wound After Extirpation of the Rectum," Proctology Research Laboratory with Clinic, Moscow, pp. 74-78, Translation of Document.

V.A. Kochnev, "Use of the Vacuum Drainage System for the Prevention of Postoperative Wound Complications in Tumor Patients," Voprosy Onkologii, vol. 13, No. 5, pp. 102-105, 1967, Translation of Document.

B.M. Mirazimov, "Free Skin Grafting of Wounds and Ulcers Using the 'Vacuum Treatment' Method," Traumatology and Orthopedic Clinic of the Second Moscow N. I. Pirogov Institute of Medicine, pp. 54-58, Translation.

B.M. Mirazimov, "Free Skin Grafting of the Foot with Preparation of the Wound Surface by Vacuum Treatment," Traumatology and Orthopedic Clinic of the Second Moscow N. I. Pirogov Institute of Medicine, pp. 19-22, Translation.

B.M. Mirazimov et al., "Microflora of Protractedly Healing Wounds and teh Effectiveness of Vacuum Treatment," Traumatology and Orthopedic Clinic of the Second Moscow N. I. Pirogov Institute of Medicine and Bacteriology Laboratory of Municipal Clinical Hospital No. 4, pp. 40-43, Translation.

B.M. Mirazimov, "Preparation of WOunds and Ulcers for Skin Grafting by Vacuum Treatment," Beitr Orthop., vol. 14 No. 4, pp. 224-230, 1967, Translation.

O.Iu. Netudykhatka, "Effect of Low-Dose Vacuum on the COurse of the Repair Process in Bony Tissue," N.I. Pirogov Odessa Institute of Medicine and Odessa Institute of Health Resort Treatment, pp. 411-415, Translation.

L.A. Volkov, "Use of the Vacuum Drainage System in Surgical Practice," University of Surgery, Blagoveshchensk Institute of Medicine, 2 pages—Translation.

H. Teder et al.,"Continuous Wound Irrigation in the Pig," Journal of Investigative Surgery, vol. 1, pp. 399-407.

Y. Nakayama, MD et al., "A New Method for the Dressing of Free Skin Grafts," Department of Plastic and Reconstructive Surgery at hte Institute of Clinical Medicine of the University of Tsukuba, pp. 1216-1219.

Y. Nakayama, MD et al., "A New Dressing Method for Free Skin Grafting in Hands," Ann. Plastic Surgery, vol. 26, pp. 499-502, 1991.

W. Fleischmann et al., "Vacuum Sealing for the Treatment of Soft Tissue Injury in Open Fractures," Unfallchirurg, vol. 96, pp. 488-492, 1993, Translation.

W. B. Brock, MD et al., "Temporary Closure of Open Abdominal Wounds: The Vacuum Pack," Department of Surgery, Chattanooga Unit, University of Tennessee College of Medicine, vol. 61 No. 1, pp. 30-35, Jan. 1995.

M. Schein et al., "The 'Sandwhich Technique' in the Management of the Open Abdomen," Br. J. Surg., vol. 73, pp. 369-370, 1986.

A. Broome, M.D. et al., "Open Treatment of Abdominal Septic Catastrophies," World Journal of Surgery, vol. 7, pp. 792-796, 1983.

A. Valenta, "Using the Vacuum Dressing Alternative for Difficult Wounds," AJN, pp. 44-45, 1994.

V. Vatanasapt, M.D.et al., Red Rubber Bulb, Cheap and Effective VAcuum Drainage, J. Med. Assoc. Thai. vol. 72 No. 4, pp. 193-197, Apr. 1989.

W.H. Brummelkamp, et al., "High-VAcuum Drainage and Primary Perineal Wound Closure in Abdominoperineal Excision of the Rectum," The Netherlands Journal of Surgery, vol. 43 No. 6, p. 236-239, 1991.

M.J. Morykwas, PhD, et al., "Nonsurgical Modalities to Enhance Healing and Care of Soft Tissue Wounds," Journal of the Southern Orthopaedic Association, vol. 6 No. 4, pp. 279-288, 1997.

Sames Cp, Sealing of OWunds with Vacuum Drainage (Letter), British Medical Journal vol. 2, p. 1223, 1977.

S.E. Greer, et al., Preliminary Results from a Multicenter, Randomized, Controlled, Study of the Use of Subatmospheric Pressure Dressing for Pressure Ulcer Healing, Wound Repair and Regeneration, vol. 7, p. 255, 1999.

S.E. Greer, et al., "The Use of Subatmosperic Pressure Dressing for the Coverage of Radial Forearm Free Flap Donorsite Exposed Tendon Complications," Annals of Plastic Surgery, vol. 43 No. 5, pp. 551-554, 1999.

S.E. Greer, et al., "Techniques for Applying Subatmosperic Pressure Dressing to Wounds in Difficult Regions of Anatomy," JWOCN, vol. 26 No. 5, 1999.

S.E. Greer, et al., "The Use of Subatmospheric Pressure Dressing to Salvage a Gustilo Grade IIIB Open Tibial Fracture with Concomitant Osteomyelitis to Avert a Free Flap," Annals of Plastic Surgery, vol. 41, p. 687, 1998.

D.G. Genecov, et al., "A Cotrolled Subatmospheric Pressure Dressing Increases the Rate of Skin Graft Donor Site Reepithelialization," Annals of Plastic Surgery, vol. 40, pp. 219-225, 1998.

S. Mendez-Eastman, "Negative Pressure Wound Therapy," Plastic Surgical Nursing, vol. 18, pp. 27-29, 1998.

P. Banwell, et al., "The Use of Negative Pressure to Promote Healing," British Journal of Plastic Surgery, vol. 51, p. 79, 1998.

J.H. Blackburn, et al., "Negative-Pressure Dressing as a Bolster for Skin Grafts," Annals of Plastic Surgery, vol. 40, pp. 453-457, 1998.

L.A. Smith, et al., "Vacuum Pack Technique of Temporary Abdominal Closure: A four-Year Experience," The American Surgeon, vol. 63 No. 12, pp. 1102-1108, 1997.

J.M. McCulloch, et al., "Vacuum-Compression Therapy for the Treatment of an Ischemic Ulcer," Physical Therapy, vol. 73, pp. 165-169, 1998.

M.T. Mrkonijie, et al., "The Use of Negative Pressure to Promote the Healing of Tissue Defects: A Clinical Trial Using the Vacuum Sealing Technique," British Journal of Plastic Surgery, vol. 50, pp. 194-199, 1997.

Registration No. 1,982,349, Owner Kinetic Concepts, Inc., Source: United States Patent and Trademark Office website. Filing date May 1, 1995, Registration date Jun. 25, 1996.

K. Eichenwald, et al., "Hidden Interest—A special Report; When Physicians Double as Entrepreneurs," The New York Times p. 1, Nov. 30, 1999.

W. Fleischmann, et al., Treatment of Bone and Soft Tissue Defects in Infected Nonunion, Acta Orthopaedica Beligica, vol. 58, pp. 227-235, 1992.

Susan Mendez-Eastmen, RN; "When Wounds Won't Heal" RN Jan. 1998, vol. 61 (1); Medical Economics Company, Inc., Montvale, NJ, USA; pp. 20-24.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," *Current Problems in Modern Clinical Surgery: Interdepartmental Collection*, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164 (copy and certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
European Search Report date mailed Jun. 5, 2002; EP Application No. 02003099.5.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

* cited by examiner

WOUND THERAPY DEVICE AND RELATED METHODS

This application is a continuation of application Ser. No. 08/517,901 filed Aug. 22, 1995; now abandoned which is a continuation-in-part of application Ser. No. 08/293,854 filed Aug. 22, 1994 now abandoned.

BACKGROUND OF THE INVENTION

1. Field of the Invention

The present invention relates to the healing of wounds and, more particularly, but not by way of limitation, to an apparatus for closing wounds that is compact, self-contained, and includes a disposable wound fluids canister.

2. Description of Background Art

Wound closure involves epithelial and subcutaneous tissue adjacent the wound migrating towards the center of the wound until it closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but are also less able to successfully fight bacterial infection and, thus are less able to close the wound naturally. Such wounds have presented difficulties to medical personnel for many years.

The most common technique for closing open wounds has been the use of sutures or staples. Although such mechanical closure techniques are widely practiced and often effective, they suffer a major disadvantage by providing tension on the skin tissue adjacent the wound. That is, the tensile force required to achieve closure using sutures or staples causes very high localized stresses at the suture or staple insertion point. Such stresses commonly result in the rupture of the tissue at those points, which can eventually cause dehiscence in wounds, providing additional tissue loss.

Moreover, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

The above problem is discussed in WO 93/09727 which proposes as a solution a procedure for draining the wound by applying a continuous negative pressure to the wound over an area sufficient to promote migration of epithelial and subcutaneous tissue toward the wound. Although WO 93/09727 deals in some detail with the clinical considerations of this kind of treatment, the apparatus described has certain practical shortcomings.

One problem with the apparatus described in the above prior document is that no means are disclosed for avoiding spread of infection from one patient to another or re-infection of the patient being treated.

SUMMARY OF THE INVENTION

It is a primary object of the present invention to provide a wound closure apparatus that closes wounds without stressing the surrounding skin.

It is another object of the present invention to render technology like that disclosed in WO 93/09727 available in a convenient, compact and self-contained, efficient and economically feasible system. It is also an object to optimize the safety and effectiveness of such a device, particularly from an infection control standpoint.

It is a further object of the present invention to provide a wound closure apparatus that includes a removable and disposable wound fluids collection canister to protect the wound closure apparatus from contamination.

In accordance with the present invention, there is provided a therapeutic apparatus for stimulating healing of wounds, said apparatus including a housing that contains a vacuum pump and a chamber for holding a disposable wound drainage collection canister. The canister preferably resides within the chamber and connects at an outlet with the vacuum pump and at an inlet with a porous pad. The pad is placed over a wound and adhesively secured thereto to create a sealed environment at the wound. Thus, when the vacuum pump activates, it evacuates air from the canister and thence the wound environment, resulting in the application of negative pressure to the wound, which in turn tends to promote drainage of fluids flowing from the wound into the canister. After the canister is filled, it is removed from the chamber, disposed of, and replaced with another canister to continue therapy.

Although the vacuum pump is designed to be reusable because of its more costly components, the apparatus utilizes a removable and disposable canister adapted to prevent contamination of the vacuum pump or the remainder of the apparatus. If the vacuum pump or other parts of the housing or the tubing leading to the pump from the canister became contaminated, the wound closure apparatus would have to be completely disassembled, thoroughly cleaned and possibly discarded. Disassembly and cleaning of the wound closure apparatus is extremely time and labor intensive, while disposal of the wound closure apparatus is expensive. Consequently, a removable and disposable canister prevents either of the above undesirable circumstances from occurring.

Still other objects, features and advantages of the present invention will become evident to those skilled in the art in light of the following drawings and description of the presently preferred embodiment.

DETAILED DESCRIPTION OF THE INVENTION

Figure 1:
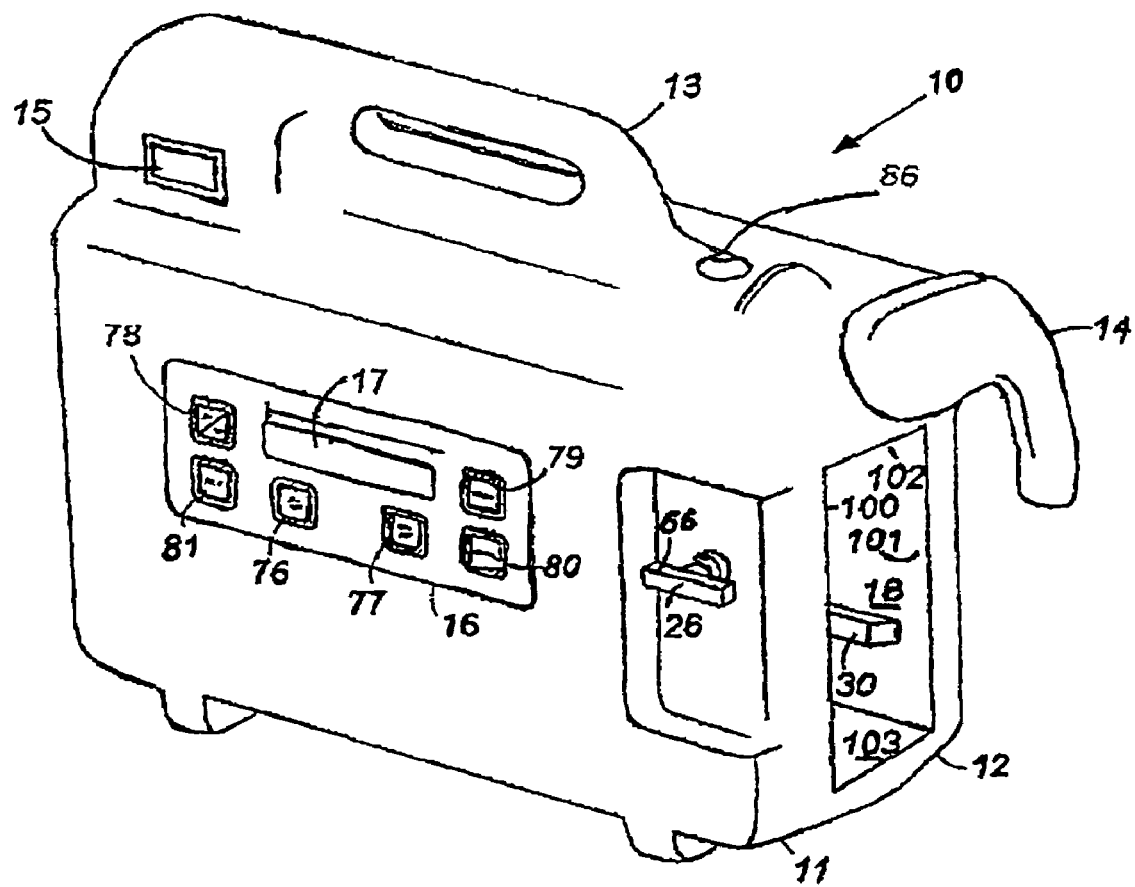
FIG. 1 is a perspective view depicting the vacuum pump unit of a wound closure apparatus constructed according to the teachings of the present invention.
Figure 2:
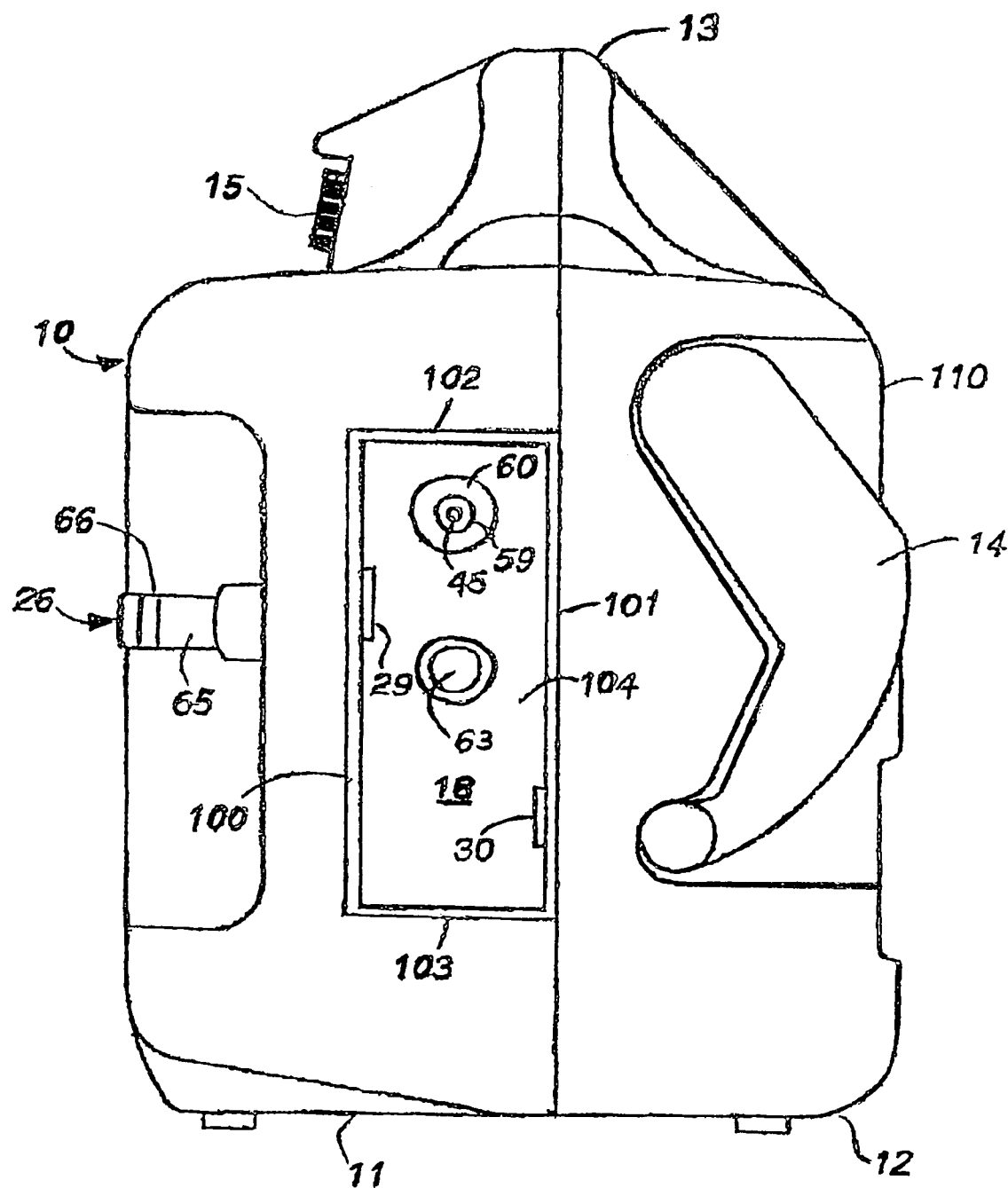
FIG. 2 is a right side plan view depicting the vacuum pump unit of FIG. 1.

As illustrated in FIGS. 1 and 2, front housing 11 and rear housing 12 connect together using any suitable means such as screws and fasteners to provide wound closure vacuum pump 10 with a small, compact, and easily portable carrying case. Consequently, front housing 11 and rear housing 12 connect together to form handle 13 that permits easy carrying of wound closure apparatus 10. Except as may be otherwise evident from this description, the carrying case of vacuum pump 10 is substantially as described and shown in WIPO Design No. DM/032185.

Figure 3:
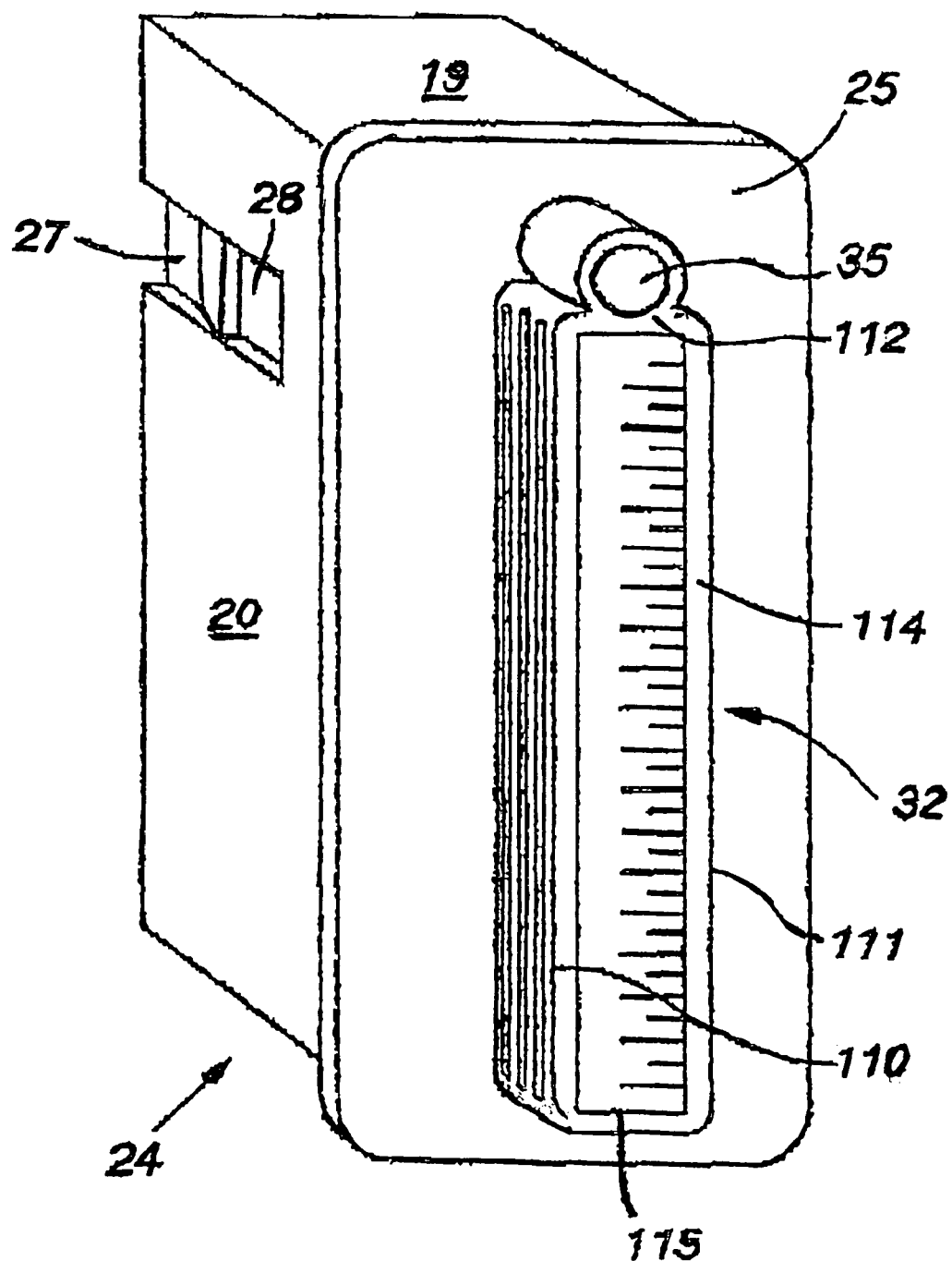
FIG. 3 is a perspective view depicting a wound drainage collection canister for use in conjunction with the vacuum pump unit of FIG. 1.
Figure 4:
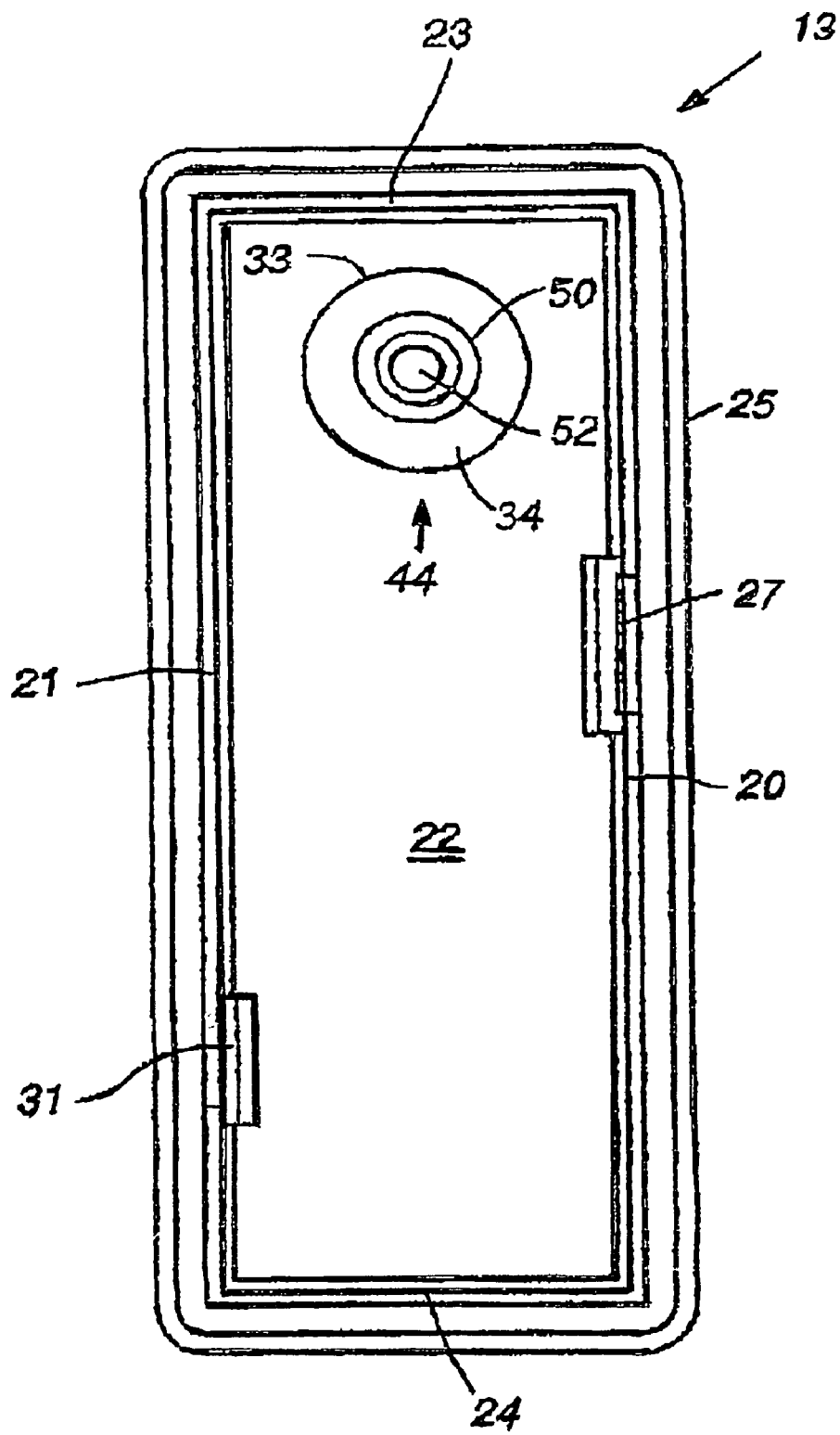
FIG. 4 is a rear plan view depicting the wound drainage collection canister of FIG. 3.
Figure 5:
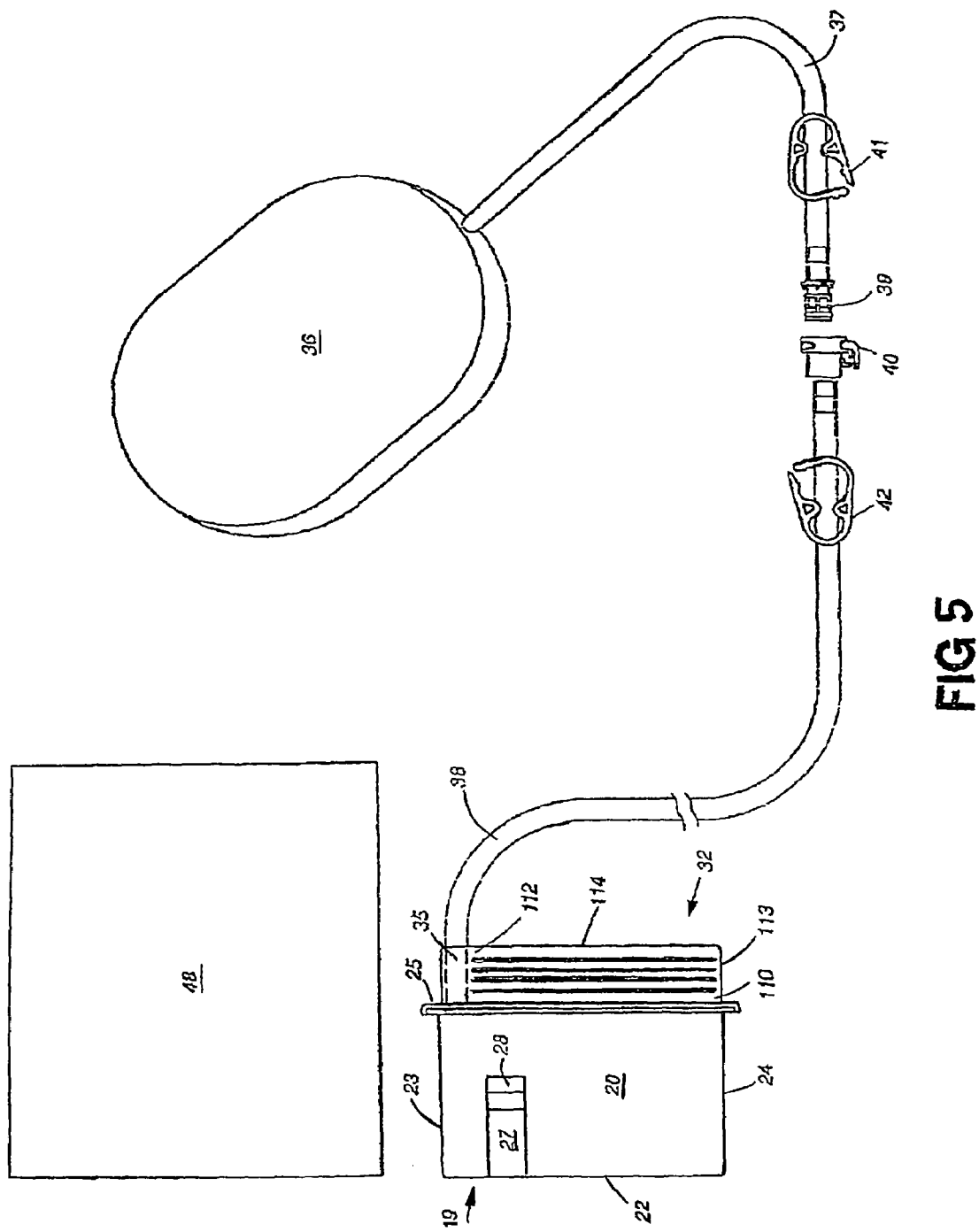
FIG. 5 is a perspective view depicting the connection of a wound drainage collection canister of FIG. 3 to a wound coverage pad.

Front housing 11 includes power switch 15 that is movable between an on and off position to permit user control of the delivery of power to wound closure apparatus 10. Keypad 16 and liquid crystal display (LCD) 17 mount to front housing 11 to permit the programming of wound closure apparatus 10. Chamber 18 is defined by integrally formed interior side walls 100 and 101, top wall 102, bottom wall 103 and rear wall 104. Side wall 100 is dependently attached to the interior of front housing 11 by standard mounting hardware (not shown). The wound fluids collection canister, illustrated in FIGS. 3-5, is received within chamber 18. Side walls 100 and 101 each include a key 29 and 30, respectively, that aid in the alignment of wound fluids collection canister 19 within chamber 18. Furthermore, front housing 11 includes latch 26 to secure the wound fluids collection canister within chamber 18.

Rear housing 12 includes arm 14 pivotally mounted to it within recess 110. An identical arm pivotally mounts to the opposite side of rear housing 12 within an identical recess. Arm 14 and its corresponding arm mounted on the opposite side of rear housing 12 pivot from within their recesses to a position where they support wound closure apparatus 10 at an angle. Arm 14 and its corresponding arm angularly support wound closure apparatus 10 to permit easier user access to keypad 16. Arm 14 and its corresponding arm may also be used to permit hanging of apparatus 10 from a hospital bed foot board.

Canister 19 has a shape as shown in FIGS. 3 to 6. As illustrated in FIGS. 3 to 6, canister 19 includes side walls 20 and 21, top wall 23, bottom wall 24, back wall 22 and front wall 25 that define the rectangular chamber for receiving blood, pus, and other fluids emitted from a wound. Side walls 20 and 21 include key ways 27 and 31 respectively, that receive a respective one of keys 29 and 30 to provide easy alignment of canister 19 within chamber 18. Furthermore, key way 27 includes recess 28 that receives latch 26 to fasten canister 19 within chamber 18.

Front wall 25 of canister 19 includes raised portion 32 extending therefrom to furnish a window that permits a user to determine the level of wound fluids within canister 19. Accordingly, raised portion 32 is transparent so that the level of wound fluids within canister 19 may be visually determined. Raised portion 32 includes side walls 110 and 111, top wall 112, bottom wall 113, and front face 114 that define a chamber which opens into the chamber defined by side walls 20 and 21, top wall 23, bottom wall 24, back wall 22 and front wall 25 of canister 19. Front face 114 of raised portion 32 includes graduations that demarcate the volume of wound fluid within canister 19. Additionally, side walls 110 and 111 of raised portion 32 include ridges that provide a gripping surface for the user during the insertion and removal of canister 19 from chamber 18.

Although raised portion 32 is transparent to permit the determination of the level of wound fluids within canister 19, side walls 20 and 21, back wall 22, top wall 23, bottom wall 24, and front wall 25 are opaque so that they are only translucent. As an alternative, the portions of canister 19 surrounding filter 46 may also be transparent. This enables a user to visually check for signs of contamination of filter 46. In this preferred embodiment, side walls 20 and 21, back wall 22, top wall 23, bottom wall 24, front wall 25, and raised portion 32 of canister 19 are fabricated from a plastic material.

Canister 19 includes inlet 35 that is formed integrally with top wall 112 of raised portion 32. Inlet 35 is cylindrical in shape and communicates with the interior of canister 19 to permit the transfer of wound fluids into canister 19. In this preferred embodiment, inlet 35 is also fabricated from a plastic material.

In order to prevent liquids sucked into the canister from splashing directly onto cap 49, which mask the outlet 44, and to reduce foaming within the canister, inlet 35 has a blind inner end. Inlet 35 has a slot 35A so that drainage fluid is deflected downwardly into the raised handle portion 32 of the canister. Handle portion 32 may communicate with the main part of the canister through one or more holes in wall 25. It is desirable to avoid foaming because this can give a false reading when a capacitance sensing device is used to sense when the canister is filled. An anti-foaming material, e.g. a silicone, may be added to the canister, e.g. by coating the interior walls. It may also be advantageous to include a gel-forming substance, e.g. a polycrylamide of modified starch in order to immobilize the drainage fluid. This is particularly useful if the apparatus is likely to be tilted.

Wound fluids (i.e. drainage) are communicated through inlet 35 into canister 19 via pad 36 and hoses 37 and 38. In this preferred embodiment, pad 36 is fabricated from an open cell polyurethane or polyether foam. Hose 37 is inserted within pad 36 by making an incision in pad 36 and inserting the end of hose 37. Hose 37 can then be secured within pad 36 using any suitable means such as an adhesive or a flange. Preferably, the foam pad is molded or formed with an elongated hole for the drainage tube which is an interference fit with the tube. The hoses are preferably made from medical grade PVC tube. Hose 38 mounts within inlet 35 using any suitable means such as an adhesive or welding. Hoses 37 and 38 include luer lock connectors 39 and 40, respectively, (or the equivalent, such as any known quick disconnect type coupling) that attach together to permit communication between hoses 37 and 38. Furthermore, hoses 37 and 38 include pinch clamps 41 and 42, respectively, that are capable of sealing their respective hose 37 or 38 to prevent the flow of wound fluids. The foam pad is preferably packaged in a sterile container together with its connector and clamp. When packaged, the clamps will be in their open condition.

The communication of wound fluids into canister 19 requires the securing of pad 36 over a wound. Pad 36 is secured over a wound using cover 43 which is fabricated from a plastic material and includes an adhesive on one side that sticks to human skin. Wound cover 43 is conveniently a surgical drape material comprising a sheet of elastomeric material coated peripherally or overall with a pressure-sensitive adhesive, such as an acrylic adhesive. The elastomeric or rubbery nature of the wound cover is important because it accommodates changes in pressure in the wound area during intermittent operation of the vacuum pump. The wound cover is preferably a polyurethane film with a removable backing sheet, i.e. of polythene to protect the adhesive surface.

A high degree of reticulation in the polymer foam is desirable to achieve good permeability when the foam is under suction. Foams having at least 90% and especially at least 95% of interconnecting cells are preferred.

Figure 10:
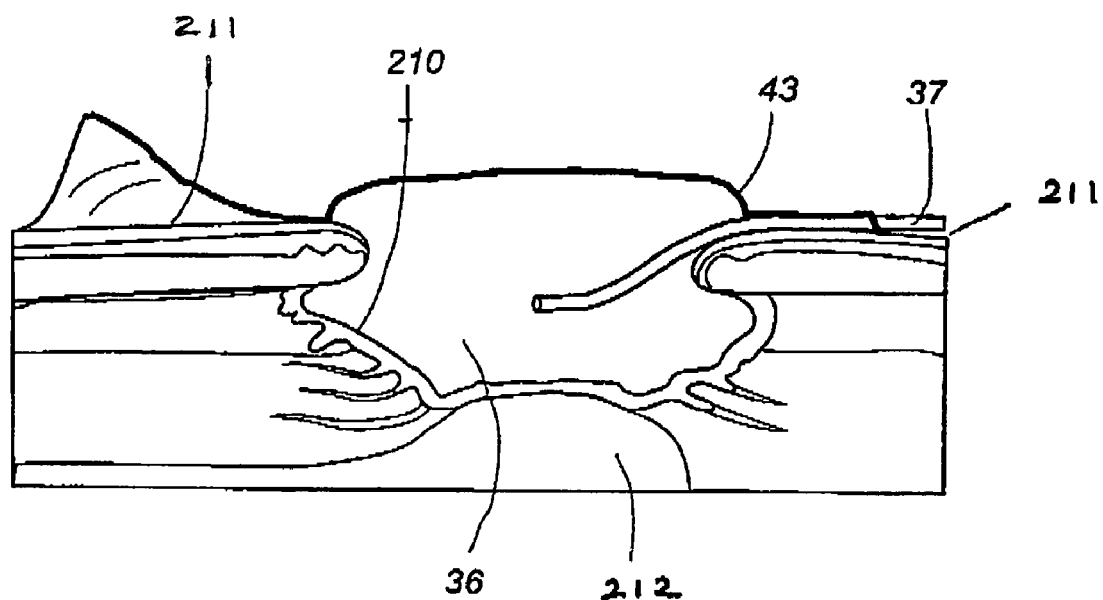
FIG. 10 is a section through a wound showing the wound pad in place.

In use, the foam pad is cut to a size which corresponds closely to the edge of the wound with the objective of packing the foam into the wound cavity 210 so that it contacts the surface of the cavity, rather than bridging the cavity. As depicted in FIG. 10, the cavity may be extensive and there may be little or no tissue coverage to the bone 212. This is illustrated diagrammatically in FIG. 10. FIG. 10 is a cross-section through a wound showing the foam pad 36 packed into the wound cavity 210. It is important that the foam should be firmly packed into the recesses of the wound cavity. Drainage tube 37 terminates within the center of the foam pad 36. Surgical drape 43 extends over the foam pad and is adhered to intact skin around the periphery of the wound. Drape 43 is also firmly adhered around the tube 37 to prevent leakage of air. A wound cover is then adhered to the surrounding skin and around the drainage tube to provide an air-tight seal around the wound.

Figure 6:
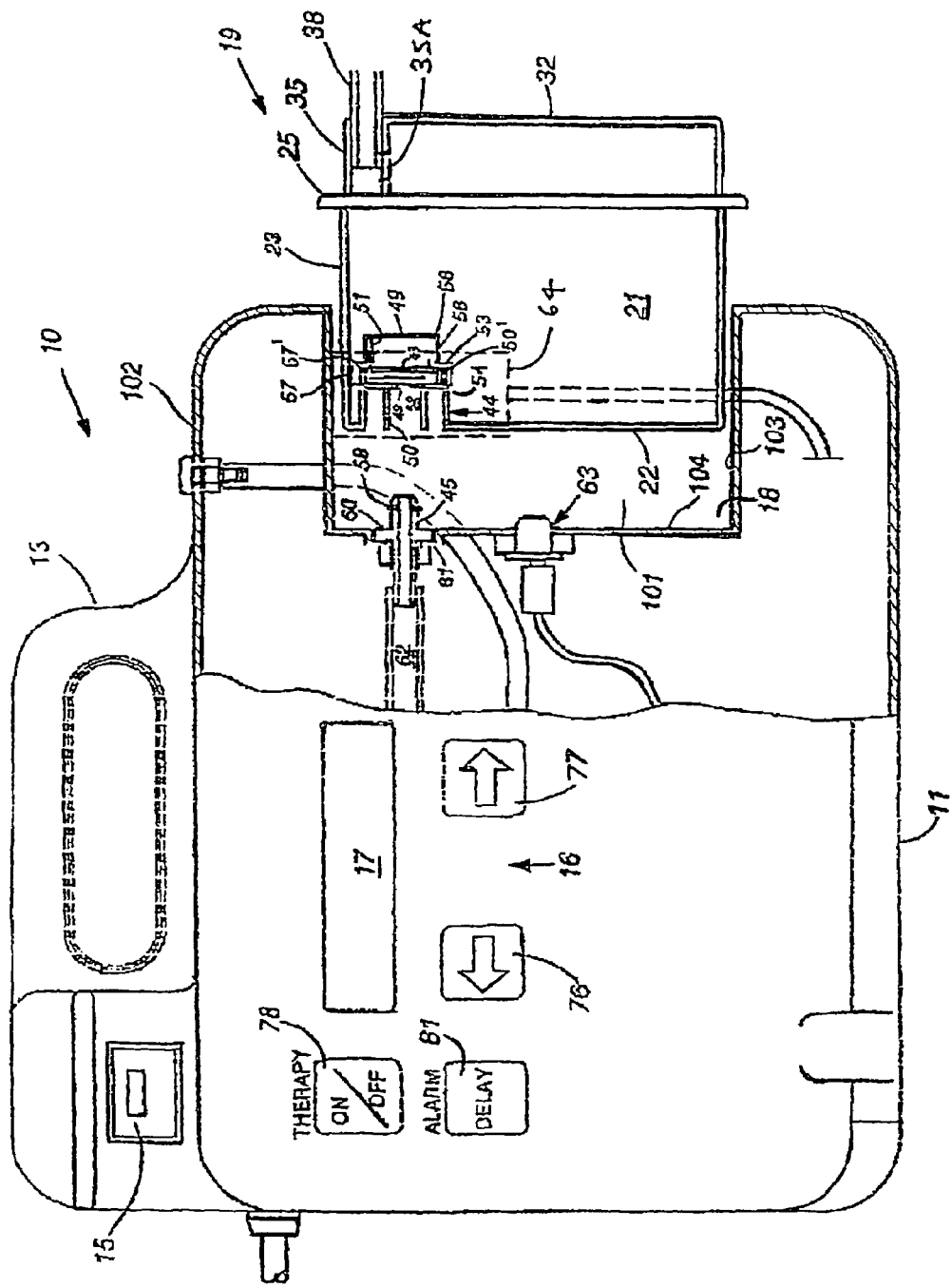
FIG. 6 is a front plan view in partial cross section depicting the connection of the wound drainage collection canister of FIG. 3 within the housing of the vacuum pump of FIG. 1.

As illustrated in FIGS. 2, 4 and 6, canister 19 includes outlet 44 that mounts over port 45 to permit wound closure apparatus 10 to draw wound fluids into canister 19. Outlet 44 is cylindrically shaped and formed as an integral part of back wall 22 by outer wall 33 and inner wall 50 which are interconnected by end wall 34. Passageway 52, defined in part by interior wall 50 and in part by filter cap 49, provides the actual conduit for outlet 44 between the interior and exterior of canister 19. The placement of canister 19 within recess 18 such that outlet 44 resides over port 45 couples canister 19 to a vacuum pump. The vacuum pump removes air from canister 19 to create vacuum pressure within canister 19. That vacuum pressure is then transmitted to a wound site through hoses 37 and 38, thereby not only enabling therapeutic use of system 10, but also tending to promote wound drainage. Any wound drainage fluid is then drawn through pad 36 and hoses 37 and 38 into canister 19.

Outlet 44 resides near top wall 23 of canister 19 to ensure efficient operation of the vacuum pump. That is, the vacuum pump removes the most air from canister 19 when the air does not have to first bubble through wound fluids contained in canister 19. Consequently, with outlet 44 positioned near the top of canister 19, the vacuum pump removes air directly from canister 19, and it is only during the final filling of canister 19 that air must bubble through wound fluids. Preferably, as described below, the apparatus includes detecting and warning means which operates before the level of drainage fluid reaches either the inlet of outlet tube so that a fresh canister can be installed.

In removing fluids from a wound utilizing wound closure apparatus 10, a major safety concern is preventing wound fluids from contaminating the vacuum pump. Accordingly, filter 46 mounts over outlet 44 utilizing filter carrier 48 and filter cap 49 to block the flow of wound fluids to outlet 44 so that wound fluids remain within canister 19 and do not flow into the vacuum pump. In this preferred embodiment, filter 46 is a 0.2 micron hydrophobic membrane filter providing a bacterial barrier, although other filters may be substituted as appropriate.

Figure 7:
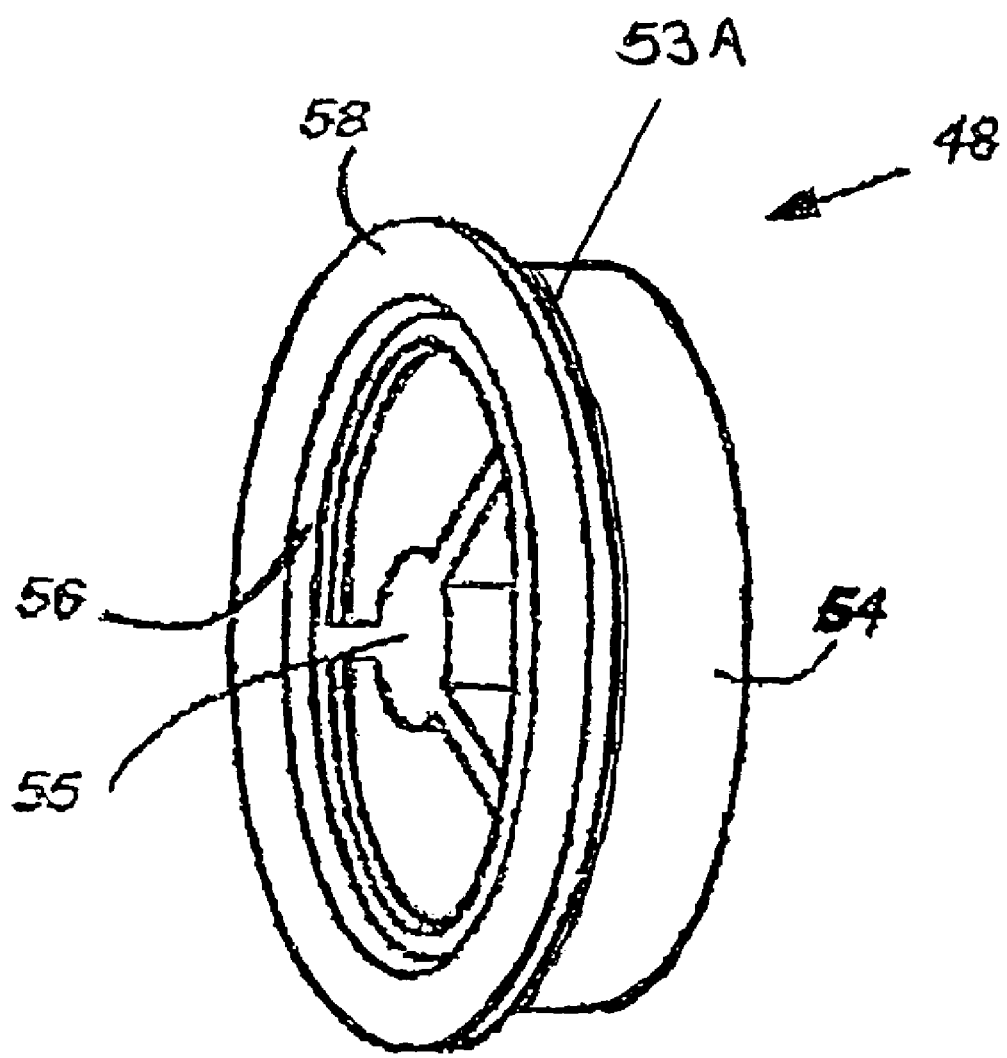
FIG. 7 is a perspective view depicting the filter carrier of the wound drainage collection canister.

As illustrated in FIG. 7, filter carrier 48 includes face 53 formed integrally with lip 54. Face 53 includes groove 56 formed therein, while lip 54 supports brace 55 in its interior. Filter 46 fits within groove 56 of face 53 and is supported within filter carrier 48 by brace 55 of lip 54. An O ring 53A is fitted in peripheral recess of filter carrier 48 to accommodate manufacturing tolerances and ensure a fluid tight seal with filter cap 49.

Figure 8:
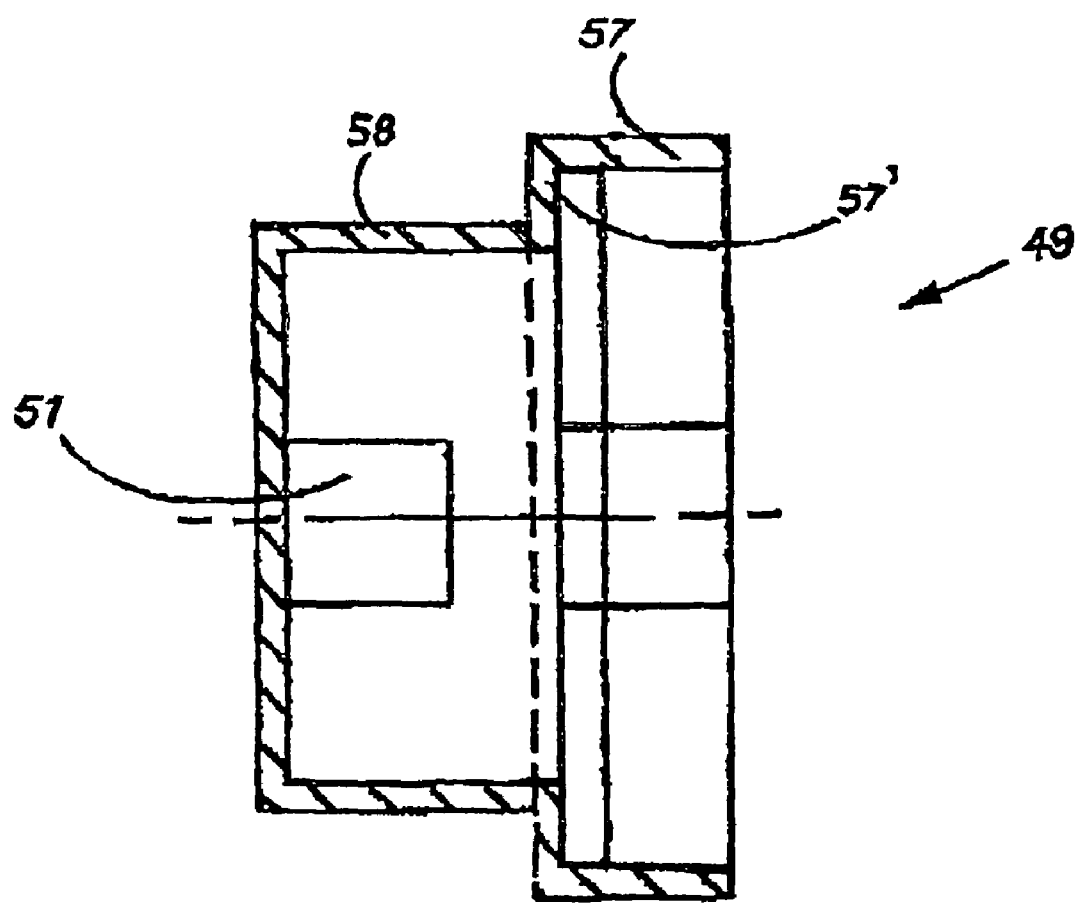
FIG. 8 is a top plan view depicting the filter cap of the wound drainage collection canister.

As illustrated in FIGS. 6 and 8, filter cap 49 includes cylindrical portions 57 and 58 which are formed integrally (with annulus 57' spanning therebetween), to hold filter carrier 48 within passageway 52 of outlet 44. To mount filter 46 over passageway 52, filter 46 is first placed within filter carrier 48 as described above. Filter carrier 48 is then positioned within filter cap 49 such that face 53 abuts annulus 57' of filter cap 49 and lip 54 of filter carrier 48 resides within annular lip 50' of outlet 44. Accordingly, when cylindrical portion 57 of filter cap 49 mounts over outlet 44, the front face 53 of filter carrier 48 and the outer edges of filter 46 abut annulus 57' to secure filter 46 within passageway 52. Filter cap 49 attaches to outlet 44 using any suitable means such as an adhesive or welding. Filter cap 49 is completely sealed except for aperture 51 positioned on top of filter cap 49. Aperture 51 communicates with port 45 via passageway 52 of outlet 44 to permit the vacuum pump to draw air from the interior of canister 19.

As illustrated in FIGS. 2 and 6, port 45 includes O-ring 59 mounted thereabout to provide a fluid tight seal between port 45 and inner wall 50 of outlet 44. Port 45 mounts through rear wall 104 of chamber 18 using any suitable means such as nuts 60 and 61. Furthermore, hose 62 attaches to the rear of port 45 using any suitable means such as a clamp to couple port 45 to the vacuum pump.

Switch 63 protrudes through rear wall 104 of chamber 18 to produce a signal indicating when canister 19 properly and securely resides within chamber 18. In this preferred embodiment, switch 63 is a normally open push button switch that mounts on rear wall 104 of chamber 18 using any suitable means such as a bracket. When canister 19 is properly positioned within chamber 18, its rear wall 22 presses the head of switch 63, closing switch 63 so that it provides a signal indicating that canister 19 properly resides within chamber 18.

Fill sensor 64 resides adjacent side wall 101, exterior to chamber 18. Fill sensor 64 provides a signal that indicates when canister 19 is filled with wound debris. In this preferred embodiment, fill sensor 64 is a capacitive sensor that mounts on side wall 101 of chamber 18 using any suitable means such as a bracket or appropriate adhesive material. Fill sensor 64 has a sensing profile 64A which determines the point at which the capacitance measurement is made.

Figure 6A:
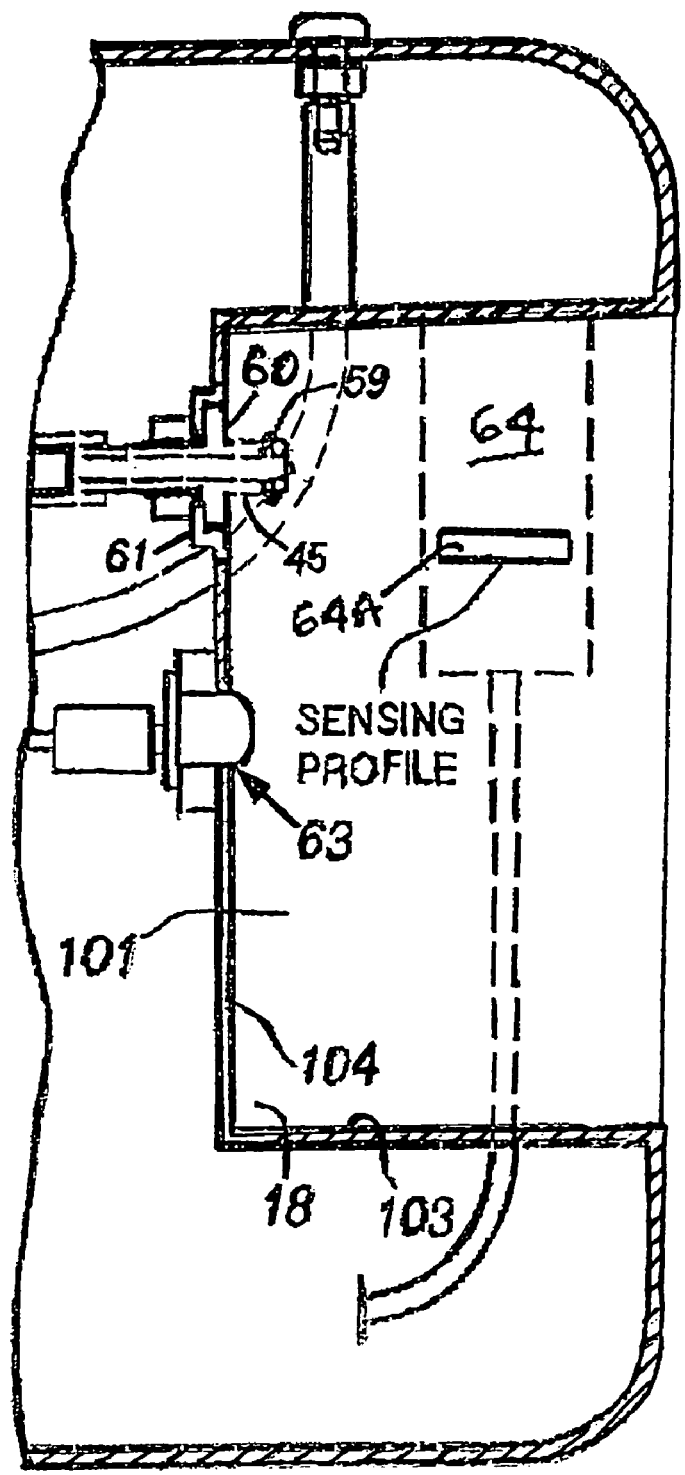
FIG. 6A is a partial view of the apparatus shown in FIG. 6 except the canister is removed.

When wound fluids have reached the level within canister 19 which corresponds to the location of the sensing profile 64A, the capacitance within canister 19 as 'seen' by fill sensor 64 changes, resulting in fill sensor 64 outputting a signal indicating that canister 19 is filled with wound fluids to the level at which the sensing profile is located. The position of this sensing profile behind wall 101 can be changed (see FIG. 6A) to provide an optimum balance of space and volume utility.

Figure 2A:
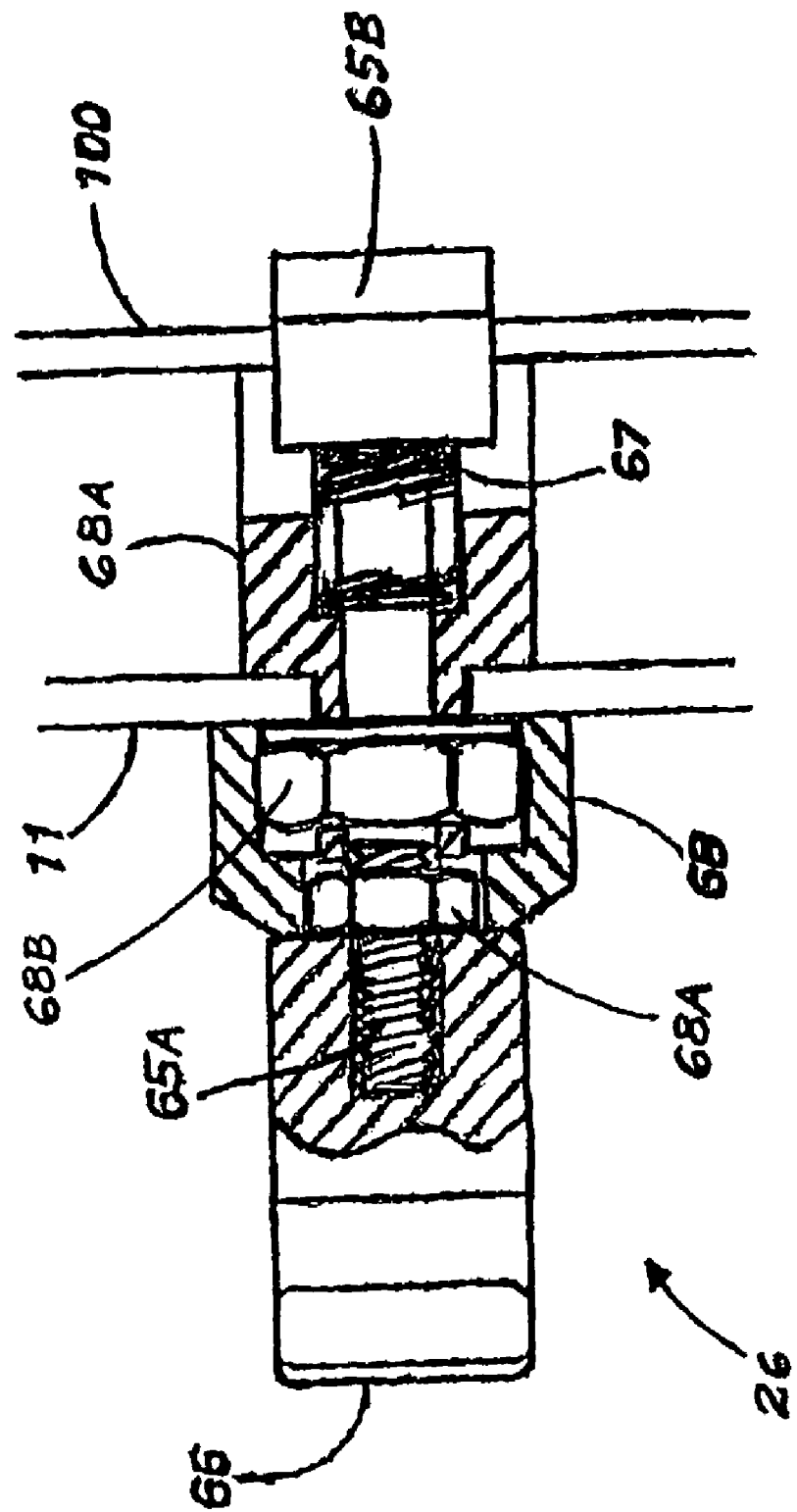
FIG. 2A is a detail view of the latch 26 portion of FIG. 2, partially cut-away to eliminate guide (or "key") 29 from the view and to show portions of latch 26 in sagital cross section.

As illustrated in FIG. 2A, latch 26 generally comprises latch pin 65, handle 66, latch guide sleeve 68A and spring 67. Latch pin 65 comprises a proximal end 65A and distal end 65B. Latch guide sleeve 68A abuts the inner surface of front housing 11 and is held securely in place from the outer side of front housing 11 by nut 68B. Handle 66 screws onto the proximal end 65A of latch pin 65 and is locked in position by nut 69A. In the preferred embodiment, cover 68 over nuts 69A and 68B provides a surface against which handle 66 abuts, thus preventing end 65B from excessively entering chamber 18 as will be understood further herein. Cover 68 also provides aesthetic enclosure of nuts 69A and 68B. Dependent attachment of side wall 100 (chamber 18), as described hereinabove, is such that side wall 100 abuts latch guide sleeve 68A on the side distal front housing 11. Further, this arrangement causes distal end 65B of latch pin 65 to project into chamber 18 under the force of spring 67 (shown partially cut away). Spring 67 resides circumferentially about latch pin 65 within an axial bore of latch pin guide 68A. Spring 67 exerts force between distal end 65B of latch pin 65 and an annulus within the axial bore of latch pin guide 68A. A transverse slot in the distal end of latch pin guide 68A receives end 65B of latch pin 65, providing rotational alignment of end 65B and further recess for end 65B when a user "pulls" handle 66 in an axial direction.

Latch 26 operates to ensure canister 19 remains secured within chamber 18. End 65B of latch 26 terminates in a point that protrudes through key 29 into chamber 18. During the placing of canister 19 within chamber 18, key way 27 of canister 19 forces the point 65B of the latch pin within key 29. However, once canister 19 has been properly positioned within chamber 18, recess 28 resides below latch pin end 65B so that spring 67 biases the point 65B of latch pin 65 into recess 28 to prevent the removal of canister 19 from chamber 18. The removal of canister 19 from chamber 18 is accomplished by grasping handle 66 and pulling the point 65B of latch pin 65 from recess 28. With the point of latch pin 65 no longer within recess 28, canister 19 may be pulled from chamber 18 using its raised portion 32.

Figure 9:
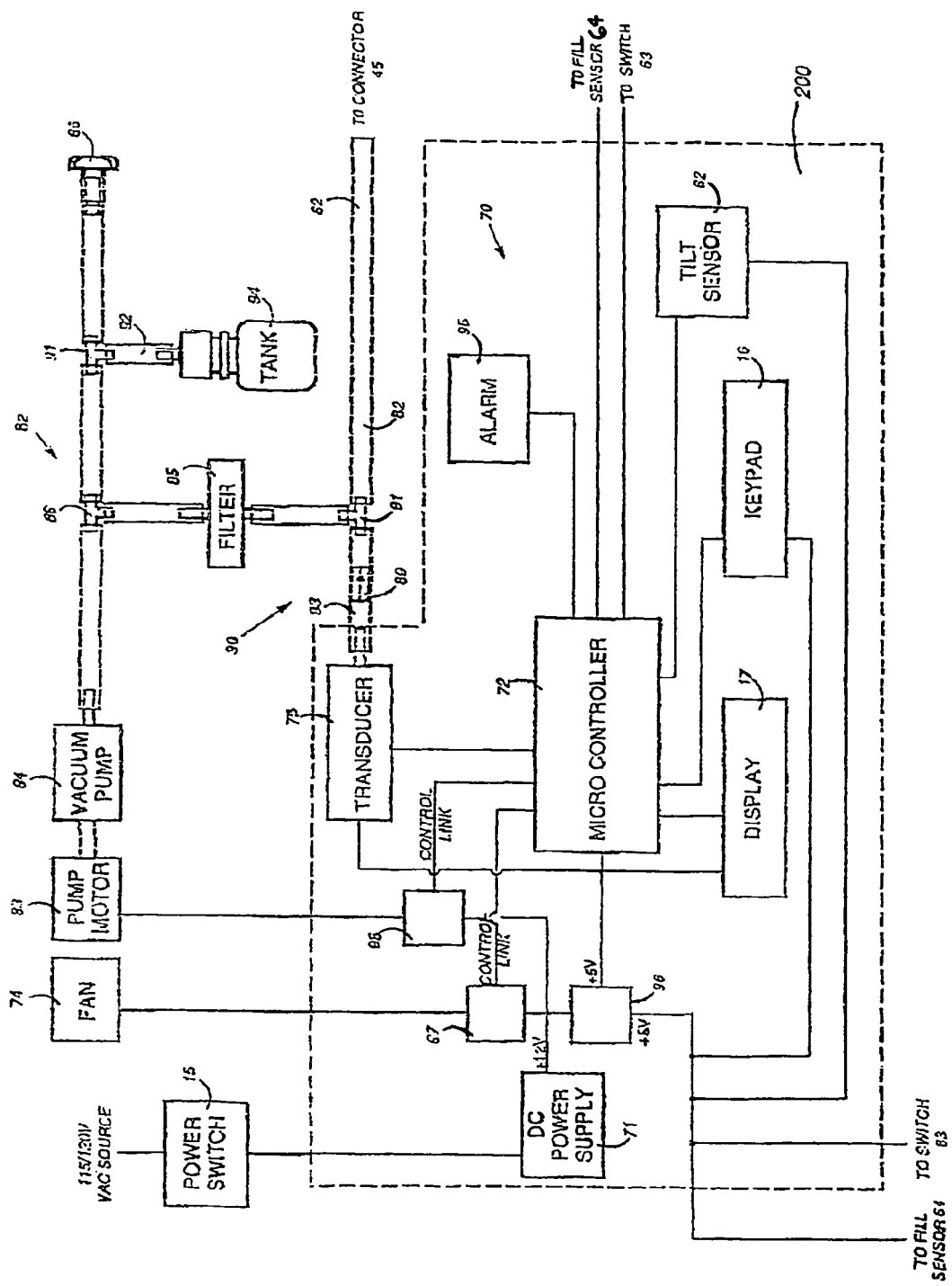
FIG. 9 is a schematic view depicting the control system for a wound closure apparatus constructed according to the teachings of the present invention.

As illustrated in FIG. 9, wound closure apparatus 10 preferably plugs into a standard 115/120 VAC power source (e.g. an outlet) to supply power to control system 70. Alternative embodiments (not shown, although similar) are readily adapted for 220 VAC power by changing the power cord and appropriately rewiring the taps of the transformer within DC power supply 71, as is readily known in the art. The application of power to control system 70 is regulated by power switch 15 which is a standard push button on/off switch. With power switch 15 depressed, DC power supply 71 receives the 115/120 VAC signal and converts it into a 12 VDC signal for use by fan 74 and motor 83. A conventional voltage regulator 96 steps down the voltage to +5V for use by each of the other DC components 16, 17, 63, 64, 72, 75 and 82. Voltage regulator 96 connects to keypad 16, LCD 17, switch 63, fill sensor 64, microcontroller 72, transducer 75, and tilt sensor 82 to supply each of them with the +5V DC signal. Microcontroller 72 links to solid state relays (MOSFETs) 97 and 98 for controlling the provision of the 12 VDC power supply to fan 74 and pump motor 83, respectively.

As illustrated in FIG. 1, once power switch 15 is depressed, a user employs keypad 16 and LCD 17 to select the operating parameters for wound closure apparatus 10. Wound closure apparatus 10 stores the previously selected operating parameters so that upon power initialization, LCD 17 displays the phrase "NEW PATIENT" with the word "NO" over arrow button 76, and the word "YES" over arrow button 77. If the user presses arrow button 76 to answer no, wound closure apparatus 10 will operate at the previously selected parameters. After answering no, the user pressures on/off button 78 to begin operation of wound closure apparatus 10.

Conversely, if the user presses arrow button 77 to indicate a new patient, wound closure apparatus 10 will operate either under default values or allow the user to select the operating parameters. To operate under default parameters, the user presses on/off button 78 after pressing arrow button 77. However, to select his or her own values, the user presses option button 79 after pressing arrow button 77.

Upon the pressing of options button 79, LCD 17 displays a bar graph representing the spectrum of available vacuum pump pressures and a numerical representation of the vacuum pump pressure presently displayed by the bar graph. The user changes vacuum pump pressure using arrow buttons 76 and 77.

The pressing of arrow button 76 reduces vacuum pump pressure, while the pressing of arrow button 77 increases vacuum pump pressure. After selecting the desired vacuum pump pressure, the user presses option button 79 to save the selected vacuum pump pressure.

Once the selected vacuum pump pressure has been saved, LCD 17 displays the pump operation times available to the user. The user may program wound closure apparatus 10 to pump either continuously or intermittently. Thus, LCD 17 displays the word "CONTINUOUS" over arrow button 76 and "INTERMITTENT" over arrow button 77. The user selects continuous operation by pressing arrow button 76 followed by on/off button 78 to activate the vacuum pump. In its continuous mode, wound closure apparatus 10 runs its vacuum pump continuously until on/off button 78 is pressed again.

If the user presses arrow button 77 to select intermittent operation, LCD 17 displays a bar graph representing the minimum and maximum on times for the vacuum pump. LCD 17 also displays the phase "ON TIME" and the numerical value presently displayed by the bar graph. A user decreases the on time of the vacuum pump by pressing arrow button 76 and increases the on time of the vacuum pump by pressing arrow button 77. After selecting the desired on time, the user presses options button 79 to save the selected on time value.

LCD 17 then displays a second bar graph representing the off time for the vacuum pump with the phrase "OFF TIME" and the numerical value presently depicted by the bar graph. Again, arrow buttons 76 and 77 are pressed to increase or decrease, respectively, the off time for the vacuum pump. After selecting the off time, the user presses options button 79 followed by on/off button 78 to operate wound closure apparatus 10 using the selected parameters.

Keypad 16 includes setting button 80 to permit the user to sequentially display the currently selected operating parameters of wound closure apparatus 10. Keypad 16 further includes delay button 81 to permit the user to deactivate an alarm sounded in response to an improper operating condition of wound closure apparatus 10. Delay button 81 provides the user with the ability to silence alarms so that the alarm will not have to be listened to during the correction of the problem.

Any new alarm conditions occurring within the fifteen minute period ("delay period") after the pressing of delay button 81 will not be indicated by an audible alarm. However, the pump will still be deactivated when appropriate, even during the delay period.

Again referring to FIG. 9, microcontroller 72 is a multi-port microprocessor with a ten-bit analog to digital ("A/D") converter having associated memory that stores the program directing microcontroller 72 during its control of wound closure apparatus 10. After receiving and storing the user selected operational parameters and receiving an on signal due to the pressing of on/off button 78, microcontroller 72 activates pump motor 83 which, in turn, drives vacuum pump 84 to begin the removal of air from canister 19.

As vacuum pump 84 operates, it draws air from within canister 19, into hose 62 via outlet 44 of canister 19 and port 45. Hose 62 connects to filter 85 and transducer 75 via T-junction 91. Filter 85 is similar to filter 46 and thus ensures no wound fluids contaminate vacuum pump 84. Filter 85 communicates with pump 84 via T-junction 88 and one arm of the latter is connected to bleed valve 86. Bleed valve 86 communicates with the atmosphere to release pressure developed within line 62 by vacuum pump 84 after microcontroller 72 deactivates vacuum pump 84. Bleed valve 86 is sufficiently small to ensure that it generally does not affect the vacuum pressure levels achieved by vacuum pump 84 as it evacuates air from canister 19, except to prevent overpressurization beyond 250 mm Hg and to prevent erratic operation of the vacuum pump at very low pressure settings.

In the preferred embodiment, an orifice of 0.5 mm diameter is especially preferred for bleed valve 86. Valve 86 or the equivalent is particularly important for enabling intermittent application of negative pressure, as the orifice 86 allows for gradual release of the negative pressure (over a period of about fifteen seconds) when the pump motor 83 is de-actuated. Bleed valve 86 is positioned outside housing 11 to facilitate un-clogging of aperture 86 in the event of a blockage. An aperture is provided in bleed valve 86, which is machined from stainless steel. Flow control orifices would be alternatives.

Line 62 also includes T-connector 91 to connect it with line 92. Line 92 is connected to tank 94 which acts as a damper to pressure changes in line 62. This dampening effect, facilitated by restrictor 89 in line 93 between transducer 75 and T-junction 91, causes the pressure measured by transducer 75 to be an accurate indication of actual wound site pressure. Transducer 75 communicates with line 62 via line 93 to measure tank 94 pressure and produce an electrical signal representative of that pressure. Transducer 75 outputs its pressure signal to microcontroller 72.

Microcontroller 72 utilizes the pressure signal to control the speed of pump motor 83. As previously described, the user selects either a default vacuum pump pressure or a desired vacuum pump pressure for the operation of wound closure apparatus 10. After receiving the wound pressure signal from transducer 75, microcontroller 72 compares the wound pressure with the user selected pressure. If the wound pressure is higher than the user selected vacuum pump pressure, microcontroller 72 reduces pump motor speed to decrease vacuum pump pressure and thus the pressure at the wound. Conversely, if the wound pressure is less than the user selected vacuum pump pressure, microcontroller 72 increases the speed of pump motor 83 resulting in an increase in the vacuum pressure applied at the wound.

Microcontroller 72 controls pump motor 83 by varying the amount of voltage received by pump motor 83. That is, microcontroller 72 receives the 12 VDC signal from DC power supply 71 and outputs a voltage between 0 and 12 VDC to pump motor 83 to control its speed in accordance with the user selected vacuum pump pressure value. Accordingly, microcontroller 72 employs feedback to ensure that the wound experiences the user selected vacuum pump pressure. If the target pressure is not reached after a period of five minutes, microcontroller 72 deactivates motor 83 and sounds the audible alarm. Additionally, the feedback signal prevents maximum vacuum pump pressure from being exceeded. If the wound pressure measured by transducer 75 exceeds a maximum safe vacuum pump pressure microcontroller 72 deactivates pump motor 83 and activates alarm 95 to signal a malfunction.

Wound closure apparatus 10 includes fan 74 to cool pump motor 83 and printed circuit ("PC") board 200 during the operation of the wound closure apparatus 10. In the preferred embodiment, microcontroller 72 controls fan 74 to always operate while power is being supplied. In alternative embodiments, however, microcontroller 72 controls fan 74 to operate only in relation to motor 83, because it is only necessary for fan 74 to operate if motor 83 is also operating. In such alternative, as long as pump motor 83 operates, microcontroller 72 runs fan 74. However, when microcontroller 72 deactivates pump motor 83 it also deactivates fan 74.

Control system 70 includes fill sensor 64 to provide a signal to microcontroller 72 that indicates when canister 19 is completely filled with wound fluids. After receiving a signal from fill sensor 64, microcontroller 72 deactivates pump motor 83 and fan 74 and activates alarm 95 to signal the user that canister 19 must be replaced.

Control system 70 includes switch 63 to prevent users from operating wound closure apparatus 10 without a canister properly installed. If a canister is not properly installed, switch 63 remains open and therefore outputs no signal to microcontroller 72. If microcontroller 72 receives no signal from switch 63, indicating no canister within chamber 18, it will not supply power to pump motor 83 even after a user has pressed on/off button 78. Furthermore, microcontroller 72 activates alarm 95 to signal the user that either a canister is not properly installed or is improperly installed within chamber 18. Microcontroller 72 operates pump motor 83 only if switch 63 is depressed to provide a signal indicating the proper placement of a canister within chamber 18.

Control system 70 includes tilt sensor 82 to prevent operation of wound closure apparatus 10 if it is tilted excessively. Excessive tilting of wound closure apparatus 10 during operation diminishes the efficiency of removal of wound fluids and, more importantly, might result in either the contamination of vacuum pump 84 or the spilling of wound fluids. Thus, if wound closure apparatus 10 tilts along any of its axes beyond a predetermined angle (approximately 45° in this preferred embodiment), tilt sensor 82 outputs a signal to microcontroller 72. In response, microcontroller 72 deactivates pump motor 83 and activates alarm 95 to signal the user of the excessive tilt situation. In this preferred embodiment, tilt sensor 82 may be implemented with any standard mercury switch. A predetermined delay (e.g. 30 seconds) may be incorporated in the circuitry so that the tilt alarm does not operate immediately.

Although the present invention has been described in terms of the foregoing presently preferred embodiment, such description has been for exemplary purposes only. There will be apparent to those of ordinary skill in the art many alternatives, equivalents and variations that will fall within the scope of the present invention. That scope, accordingly, is not to be limited in any respect by the foregoing description; rather, it is defined only by the claims which follow.

What is claimed is:

1. A therapeutic combination of promoting tissue healing, comprising:
    a porous pad which is permeable to fluids;
    a tube having a first end in fluid communication with said porous pad;
    a canister for collecting fluids drawn through said tube, said canister being fluidly connected with a second end of said tube which is opposite the first end of said tube, wherein said canister is removably received in a recess in a housing;
    a suction pump for applying negative pressure to said tube, said suction pump being fluidly connected to said canister;
    at least one bacterial filter between said canister and said suction pump;
    an elastomeric film dressing having a pressure-sensitive adhesive in peripheral areas for securing said porous pad to tissue within a sealed space;

a sensor for detecting when said canister is substantially full with fluid, said sensor being associated with said suction pump to discontinue application of the negative pressure when a substantially full condition of said canister is detected; and a switch providing a signal indicating that the canister properly resides within the recess when the switch is pressed.

2. A therapeutic combination as claimed in claim 1 wherein the housing houses said suction pump.

3. A therapeutic combination as claimed in claim 1 wherein said tube is fitted as an interference fit into an interior portion of said porous pad.

4. A therapeutic combination as claimed in claim 1 wherein said porous pad comprises a polymer foam having interconnecting cells.

5. A therapeutic combination as claimed in claim 4 wherein said polymer foam is a polyether reticulated foam having at least 95% interconnecting cells.

6. A therapeutic combination as claimed in claim 1 wherein said porous pad comprises a reticulated foam having at least 90% interconnecting cells.

7. A therapeutic combination as claimed in claim 1 wherein said porous pad comprises a reticulated foam having at least 95% interconnecting cells.

8. A therapeutic combination as claimed in claim 1 further comprising a tilt sensor for determining tilting of said therapeutic combination beyond a predetermined angle, said tilt sensor being associated with said suction pump to discontinue application of the negative pressure when tilting of said therapeutic combination beyond said predetermined angle is detected.

9. The therapeutic combination of claim 1, wherein the peripheral areas with the pressure-sensitive adhesive extend beyond a periphery of the porous pad for adhering to intact skin around a wound.

10. A therapeutic combination of promoting tissue healing, comprising:
    a porous pad which is permeable to fluids;
    a tube having a first end in fluid communication with said porous pad;
    a canister for collecting fluids drawn through said tube, said canister being fluidly connected with a second end of said tube which is opposite the first end of said tube, wherein said canister is removably received in a recess in a housing;
    a suction pump for applying negative pressure to said tube, said suction pump being fluidly connected to said canister;
    at least one bacterial filter between said canister and said suction pump;
    an elastomeric film dressing having a pressure-sensitive adhesive in peripheral areas for securing said porous pad to tissue within a sealed space;
    a tilt sensor for determining tilting of said therapeutic combination beyond a predetermined angle, said tilt sensor being associated with said suction pump to discontinue application of the negative pressure when tilting of said therapeutic combination beyond said predetermined angle is detected; and
    a switch providing a signal indicating that the canister properly resides within the recess when the switch is pressed.

11. A therapeutic combination as claimed in claim 10 wherein said tube is fitted as an interference fit into an interior portion of said porous pad.

12. A therapeutic combination as claimed in claim 10 wherein said porous pad comprises a polymer foam having interconnecting cells.

13. A therapeutic combination as claimed in claim 10 wherein said porous pad comprises a reticulated foam having at least 90% interconnected cells.

14. A therapeutic combination of promoting tissue healing, comprising:
    a porous pad which is permeable to fluids;
    a tube having a first end in fluid communication with said porous pad;
    a canister for collecting fluids drawn through said tube, said canister being fluidly connected with a second end of said tube which is opposite the first end of said tube, wherein said canister is removably received in a recess in a housing;
    a suction pump for applying negative pressure to said tube, said suction pump being fluidly connected to said canister;
    at least one bacterial filter between said canister and said suction pump;
    an elastomeric film dressing having a pressure-sensitive adhesive in peripheral areas for securing said porous pad to tissue within a sealed space;
    a sensor for detecting when said canister is substantially full with fluid, said sensor being associated with said suction pump to discontinue application of the negative pressure when a substantially full condition of said canister is detected;
    a tilt sensor for determining tilting of said therapeutic combination beyond a predetermined angle, said tilt sensor being associated with said suction pump to discontinue application of the negative pressure when tilting of said therapeutic combination beyond said predetermined angle is detected; and
    a switch providing a signal indicating that the canister properly resides within the recess when the switch is pressed;
    wherein said porous pad comprises a reticulated foam having at least 90% interconnecting cells; and
    wherein the peripheral areas with the pressure-sensitive adhesive extend beyond a periphery of the porous pad for adhering to intact skin around a wound.

15. A therapeutic combination as claimed in claim 1 further comprising:
    a latch securing the canister in the recess in the housing.

16. A therapeutic combination as claimed in claim 1, wherein the canister includes a transparent window.

17. A therapeutic combination as claimed in claim 8, wherein the predetermined angle is about 45 degrees.

* * * * *